United States Patent
Fattori et al.

(10) Patent No.: US 7,065,821 B2
(45) Date of Patent: Jun. 27, 2006

(54) POWERED TOOTHBRUSH

(75) Inventors: Joseph Edward Fattori, Mendham, NJ (US); Alan Vincent Sorrentino, Cranbury, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/700,598

(22) Filed: Nov. 4, 2003

(65) Prior Publication Data

US 2004/0158944 A1    Aug. 19, 2004

Related U.S. Application Data

(60) Provisional application No. 60/423,873, filed on Nov. 5, 2002.

(51) Int. Cl.
*A46B 13/00* (2006.01)
(52) U.S. Cl. .......................... 15/22.2; 15/22.1
(58) Field of Classification Search ................. 15/21.1, 15/22.1, 22.2, 22.4, 28
See application file for complete search history.

(56) References Cited

U.S. PATENT DOCUMENTS

| | | | |
|---|---|---|---|
| 3,196,298 A * | 7/1965 | Kent | 310/50 |
| 3,379,906 A * | 4/1968 | Spohr | 310/50 |
| 3,551,931 A * | 1/1971 | Monroe et al. | 15/22.1 |
| 4,783,869 A | 11/1988 | Lee | |
| 5,381,576 A * | 1/1995 | Hwang | 15/22.1 |
| 5,383,242 A * | 1/1995 | Bigler et al. | 15/22.1 |
| 5,448,792 A * | 9/1995 | Wiedemann et al. | 15/22.1 |
| 6,347,425 B1 | 2/2002 | Fattori et al. | |
| 6,371,294 B1 | 4/2002 | Blaustein et al. | |
| 6,453,498 B1 * | 9/2002 | Wu | 15/22.1 |
| 6,581,233 B1 * | 6/2003 | Cheng | 15/28 |

* cited by examiner

*Primary Examiner*—Richard Crispino
*Assistant Examiner*—Laura C Guidotti
(74) *Attorney, Agent, or Firm*—Harris A. Wolin

(57) ABSTRACT

A powered toothbrush provides movement of cleaning elements which replicate the preferred method of cleaning teeth, namely up-and-down movement on the surface of the user's teeth. This preferred movement is obtained by translating rotational movement of a motor, first into reciprocation movement within the toothbrush through the interaction of a cam follower and helical tracks, and then translation of the reciprocating movement into oscillating movement of the cleaning elements through a limited arc. The translation of rotational to reciprocating movement is achieved through interaction of a cam follower in a helical track. The translation of reciprocating movement to oscillating movement is achieved through reciprocating movement of a volute through a mating groove in the head of the toothbrush.

12 Claims, 1 Drawing Sheet

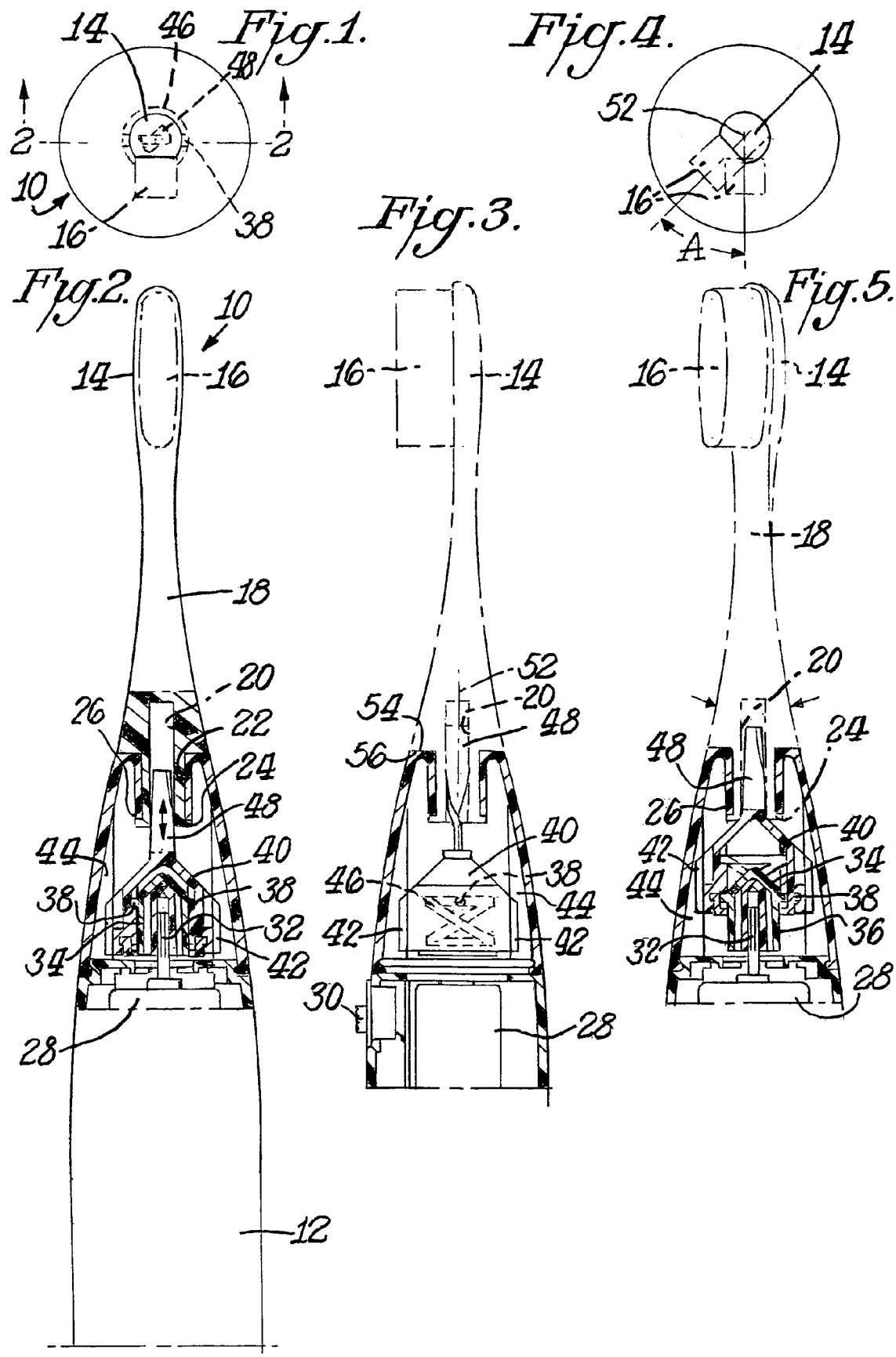

POWERED TOOTHBRUSH

This application claims the benefit of Provisional Application No. 60/423,873, filed Nov. 5, 2002.

BACKGROUND OF THE INVENTION

The current invention relates to electrically operated toothbrushes in which the rotary motion of an electric motor is converted to oscillating motion of the toothbrush head along the axis of the brush handle by multiple means including a helical groove in one part of the toothbrush which guides a cam follower in another part of the toothbrush.

Different approaches to movable toothbrush heads are to be found in the prior art. U.S. Pat. No. 4,783,869 discloses a manual toothbrush head mounted on a reciprocating and oscillating shaft. Motion is imported to the head by the user's brushing movements. More particularly, as the user brushes his/her teeth right-to-left, the toothbrush head automatically moves up and down on his/her teeth. This translation of movement is achieved through a web-shaped groove cut into an internal part of the toothbrush handle that mates with a projection on a movable shaft attached to the toothbrush head (FIGS. 3–6). As the shaft moves left and right, the interaction of groove and projection translates that movement into up-and-down movement of the toothbrush head.

U.S. Pat. No. 6,347,425 B1 describes another approach to imparting movement to a toothbrush head in which rotational movement of a motor is translated into reciprocating side-to-side and rocking up-and-down motion of a toothbrush head. This translation of movement is achieved by an offset in a powered shaft which interacts with a groove in a floating head (FIGS. 3–4).

Another apparatus for imparting movement to a toothbrush head is disclosed in U.S. Pat. No. 6,371,294B1 issued Apr. 16, 2002. In this patent, power is transmitted from a motor to the head through a series of gears. Rotational (FIG. 4) or oscillating (FIG. 12) motion is imparted to the head.

SUMMARY OF THE INVENTION

The present invention provides a brush head similar to conventional manual brushes which oscillates through a partial arc along the axis of the handle. The motion of the brush head of the present invention most closely resembles the original way individuals were taught to brush by their dentists, namely, in an up-and-down motion. The motion of the brush head provides superior interdental cleaning.

This hygienically preferred motion is imparted to the brush head utilizing a unique helical track in a portion of the powered toothbrush that translates rotational motion of a motor into movement of the head in directions perpendicular to the toothbrush axis. More specifically, the toothbrush includes a handle portion containing the rotational power source, for example, a motor powered by batteries or stepped-down house current. The motor is fixedly attached, for example, via a splined shaft, to a housing having one or more cam followers extending outwardly from its outer surface. Overlying the first housing is a second housing which can reciprocate relative to the axis of the motor. Reciprocating movement of the housing is facilitated by a helical track on the inside surfaces of the housings. The outwardly extending cam followers of the first housing attached to the motor drive shaft rotate within the helical track. As the cams move along the track, they cause the second housing to reciprocate along the axis of the toothbrush.

A toothbrush head, preferably replaceable, is connected to the reciprocating second housing through a volute. When power is applied to the motor through, for example, a switch in the toothbrush handle, the toothbrush head will oscillate back and forth through a limited arc about the longitudinal axis of the toothbrush, thereby replicating the up-and-down motion of tooth cleaning recommended by dentists.

DESCRIPTION OF THE DRAWINGS

FIG. 1 is a top plan view of a powered toothbrush with a head having a sweeping oscillating motion.

FIG. 2 is a fragmental front view of a powered toothbrush in partial cross section taken along the line 2—2 of FIG. 1.

FIG. 3 is a fragmental side elevational view of the powered toothbrush of FIGS. 1 and 2.

FIG. 4 is a top plan view of the powered toothbrush showing degree of sweep and oscillation of the head; and FIG. 5 is a front elevational view of the toothbrush of FIG. 4.

DETAILED DESCRIPTION

The powered toothbrush 10 of this invention includes a handle 12 and toothbrush head 14. Head 14 contains cleaning elements 16 which may be arranged in a variety of patterns and types. Any suitable form of cleaning elements may be used as the cleaning elements 16 in the broad practice of this invention. The term "cleaning elements" is intended to be used in a generic sense which could include conventional fiber bristles or massage elements or other forms of cleaning elements such as elastomeric fingers or walls arranged in a circular cross-sectional shape or any type of desired shape including straight portions or sinusoidal portions. Where bristles are used, the bristles could be mounted to tuft blocks or sections by extending through suitable openings in the tuft blocks so that the base of the bristles is mounted within or below the tuft block.

The toothbrush head 14 is preferably configured to allow replacement thereof. More particularly, the stem 18 of head 14 contains an elongated groove 20 or other opening along its axis. This enables inward flexure of the lower portion 22 of stem 18 when pinching pressure is exerted thereon as represented by the arrows in FIG. 5. That pressure causes inward movement of radial detents 24 at the bottom of stem 18. The detents 24 are normally biased in a radially outward direction so that they lock the head 14 onto a conical upper portion 26 of handle 12.

The desired oscillating up-and-down movement of head 14 is achieved as follows. The motive force for this movement is supplied by a motor electrically connected to a power source such as batteries or a rechargeable power pack (not shown). The motor is controlled by a switch 30 which selectively interconnects the power source with motor 28. The drive shaft 32 of motor 28 is fixedly connected, by splines or other means, to a rotatable first housing 34 which has a generally cylindrical wall 36. Extending radially outwardly from the wall 36 is a cam follower 38. Housing 34 rotates at the same speed as the drive shaft 32 to which it is fixedly connected, causing cam follower 38 to rotate at a slightly higher linear speed.

Overlying housing 34 is a second housing 40 which does not rotate. Vertical u-shaped guides 42 are opposingly positioned on the outer perimeter of housing 40 overlying fixed ribs 44 on the inside of the upper portion 26 of handle 12. In this arrangement, the second housing can move up and down along the longitudinal axis of the toothbrush, but does not rotate. That up-and-down movement of second housing 40 is achieved by movement of cam follower 38 in a helical path 46 formed on the inner surface of second housing 40 (See FIG. 3). As follower 38 rotates on first housing 34, it passes around helical path 46 on the inner periphery of second housing 40. But the housing 40 does not rotate. Therefore, as the follower 38 transverses the helical path 46, it causes the second housing to rise and fall along ribs 44 on the inside of the upper handle housing 26. This interaction of cam follower 38 within helical path 46 thereby translates rotational movement of the motor into up-and-down, or reciprocating, movement of second housing 40.

This up-and-down movement is then translated into oscillating movement of cleaning elements 16 on toothbrush head 14 as follows. Attached to the top of housing 40 is a volute member 48 which slides within a mating opening 20 in the lower end of stem 18 on head 14. As upper housing 40 moves (reciprocates) upward along the longitudinal axis of toothbrush 10, the volute 48 imparts rotational movement to stem 18 of head 14 as it twists through slot 20 in the base of the stem. Stem 18 and head 14 are free to rotate around the longitudinal axis 52 of the toothbrush axis (See FIG. 4). This rotation is facilitated by the mating surfaces 54 and 56 on the stem 18 and handle 12 which can be polished to provide a smooth surface. Optionally, a washer, for example a TEFLON® washer, can be inserted between these surfaces to facilitate the desired rotational movement of stem 18 and cleaning elements 16 relative to handle 12.

As second housing 40 moves upward toward the top of its travel, the curve of volute 48 causes stem 18 to rotate through an arc "A" shown in FIG. 5. As the first housing 34 continues to rotate, the movement of cam follower 38 in helical path 46 causes the second housing to move downward as shown in the Figures. As the second housing moves down, volute 48 moves vertically within groove 20 to rotate stem 18 and cleaning elements 16 back through angle A to its starting point (See FIGS. 2 and 4). As the motor continues to turn the cam follower 38 traveling in helix path 46, will again cause the upper housing 40 to start its upward movement which, in turn causes stem 18 and cleaning elements 16 to start turning again. This repetitive up-and-down movement of upper housing 40 is translated into up and down movement of cleaning elements on the toothbrush user's teeth.

What is claimed is:

1. A powered toothbrush comprising a handle, a head with cleaning elements thereon movable relative to the handle, a motor with a drive shaft, a first housing fixedly connected to the drive shaft having a first cam device thereon, a second housing having a non-rotational second cam device cooperatively engaged with the first cam device on the first housing to convert rotational movement of the first housing into reciprocating motion of the second housing along the longitudinal axis of the toothbrush, an extension of the second housing cooperatively mating with an opening in a portion of the head for translating reciprocating movement of the second housing into oscillating motion of the cleaning elements about the longitudinal axis of the toothbrush.

2. The powered toothbrush of claim 1 wherein the first and second cam devices on the housings are a cam follower and mating helical track for the cam follower.

3. The powered toothbrush of claim 2, wherein the cam follower is disposed on the first housing and the mating helical track is disposed on the second housing.

4. The powered toothbrush of claim 1 wherein the head of the toothbrush is removable.

5. The powered toothbrush of claim 1 wherein the handle includes an upper conical enclosure surrounding the first and second housings, the conical enclosure having an upper sliding surface.

6. The powered toothbrush of claim 5 wherein the head includes a stem with a lower sliding surface that facilitates movement across the upper sliding surface on the upper conical enclosure of the handle.

7. A powered toothbrush comprising a handle, a head with cleaning elements thereon movable relative to the handle, a motor with a drive shaft, a first housing fixedly connected to the drive shaft having a first cam device thereon, a second housing having a non-rotational second cam device cooperatively engaged with the first cam device on the first housing to convert rotational movement of the first housing into reciprocating motion of the second housing along the longitudinal axis of the toothbrush, a volute extension of the second housing cooperatively mating with an opening in a portion of the head to translate reciprocating movement of the second housing into oscillating motion of the cleaning elements about the longitudinal axis of the toothbrush.

8. The powered toothbrush of claim 7 wherein the first and second cam devices on the housings are a cam follower and mating helical track for the cam follower.

9. The powered toothbrush of claim 8, wherein the cam follower is disposed on the first housing and the mating helical track is disposed on the second housing.

10. The powered toothbrush of claim 7 wherein the head of the toothbrush is removable.

11. The powered toothbrush of claim 7 wherein the handle includes an upper conical enclosure surrounding the first and second housings, the conical enclosure having an upper sliding surface.

12. The powered toothbrush of claim 11 wherein the head includes a stem with a lower sliding surface that facilitates movement across the upper sliding surface on the upper conical enclosure of the handle.

* * * * *